United States Patent [19]

Stille

[11] 4,424,312

[45] Jan. 3, 1984

[54] PREPARATION OF AMINO ACIDS IN HIGH OPTICAL YIELD VIA CATALYTIC HYDROGENATION

[75] Inventor: John K. Stille, Fort Collins, Colo.

[73] Assignee: Polymer Sciences Corporation, New York, N.Y.

[21] Appl. No.: 243,747

[22] Filed: Mar. 16, 1981

[51] Int. Cl.$^3$ .................... C08F 8/42; C08F 220/34
[52] U.S. Cl. ........................... 525/274; 525/326.7; 525/370; 526/263; 502/159; 502/162
[58] Field of Search ............... 526/263; 525/336, 360, 525/326.7

[56] References Cited

U.S. PATENT DOCUMENTS 2,728,739 12/1955 Jones .................................. 526/263

Primary Examiner—Harry Wong, Jr.
Attorney, Agent, or Firm—Pennie & Edmonds

[57] ABSTRACT

Two new optically active pyrrolidinephosphine monomers prepared by the reaction of 2(S), 4(S)-4-diphenylphosphino-2-diphenylphosphinomethylpyrrolidine and 2(R), 4(R)-4-diphenylphosphino-2-diphenylphosphinomethylpyrrolidine with acryloyl-chloride to give N-acryloyl-2(S), 4(S)-4-diphenylphosphino-2-diphenylphosphinomethylpyrrolidine (1) and N-acryloyl-2(R), 4(R)-4-diphenylphosphino-2-diphenylphosphinomethylpyrrolidine (2). Copolymerization of 1 and 2 with hydrophilic comonomers and a divinyl monomer provided crosslinked insoluble polymers containing about 3–5% of 1 or 2 that would swell in polar solvents. Exchange of rhodium(I) onto the polymer gave catalysts which were active for the asymmetric hydrogenation of N-acyl-amino acids in high optical yields, the phosphine derived from the enantiomer of the naturally occurring 4-hydroxyproline giving S-amino acids.

2 Claims, No Drawings

PREPARATION OF AMINO ACIDS IN HIGH OPTICAL YIELD VIA CATALYTIC HYDROGENATION

BACKGROUND OF THE INVENTION

Pyrrolidinephosphine-rhodium catalysts have proven to be useful for the hydrogenation of many unsaturated substrates, and especially for the reduction of dehydroamino acids in optical yields exceeding 90%. For a review see Achiwa, K. "Fundemental Research in Homogeneous Catalysis, Vol. III", Tsutsui, M. Ed; Plenum: New York, 1979; p 549. Unfortunately, the predominant enantiomer formed has the R configuration rather than the S configuration of naturally occurring amino acids, and enantiomeric pyrrolidinephosphines whose use would result in the production of S amino acids are not readily available.

In previous papers there was described an optically active monomer, 2-p-styryl-4,5-bis(tosyloxymethyl)-1,3-dioxolane, which could be polymerized with a variety of comonomers to provide polymer attached optically active ligands for rhodium catalyzed hydroformylation and hydrogenation reactions that gave optically active aldehydes and amino acids. Part IV. Fritschel, S. J.; Ackerman, J. J. H.; Keyser, T.; Stille, J. K. *J. Org. Chem.* 1979, 44, 3152; Takaishi, N.; Imai, H.; Bertelo, C. A.; Stille, J. K. *J. Am. Chem Soc.* 1978, 100, 264; Masuda, T.; Stille, J. K. *J. Am. Chem. Soc.* 1978, 100, 268. The polymer supported catalysts achieved the same enantioselectivity as their homogeneous counterparts, were able to be recycled by simple filtration, and resued without a significant loss of activity.

At the time that the work reported herein was being completed, another polymer supported optically active phosphine catalyst, prepared by the copolymerization of 1-(4-vinylbenzoyl)-2-(S),4(S)-2-diphenylphosphino-4-diphenylphosphinomethylpyrrolidine with hydroxyethyl methacrylate, was described. Achiwa, K. *Chem. Lett.* 1978, 905. While this system was able to catalyze the reduction of itaconic acid to methyl succinic acid in about the same optical yield as the homogeneous analog (82 vs. 89% o.y.), the reduction of Z-acetamidocinnamic acid to N-acetyl phenylalanine proceeded in far lower optical yield (23 vs. 91% o.y.) with the polymer supported catalyst. When the rhodium(I) species bound to the polymer was changed from a neutral to a cationic species, the optical yield for the cinnamic acid hydrogenation was raised to 70%, still far below the results obtained with the homogeneous catalyst.

SUMMARY OF THE INVENTION

The present invention is directed to two new optically active pyrrolidinephosphine monomers prepared by the reaction of 2(S), 4(S)-4-diphenylphosphino-2-diphenylphosphinomethylpyrrolidine and 2(R), 4(R)-4-diphenylphosphino-2-diphenylphosphinomethylpyrrolidine with acryloyl-chloride to give N-acryloyl-2(S), 4(S)-4-diphenylphosphino-2-diphenylphosphinomethylpyrrolidine (1) and N-acryloyl-2(R), 4(R)-4-diphenylphosphino-2-diphenylphosphinomethylpyrrolidine (2). Copolymerization of 1 and 2 with hydrophilic comonomers and a divinyl monomer provided crosslinked insoluble polymers containing about 3-5% of 1 or 2 that would swell in polar solvents. Exchange of rhodium(I) onto the polymer gave catalysts which were active for the asymmetric hydrogenation of N-acyl-amino acids in high optical yields, the phosphine derived from the enantiomer of the naturally occurring 4-hydroxyproline giving S-amino acids. The catalysts could be reused with no loss in selectivity by simple filtration.

The present invention is thus also directed in part to the preparation of optically active pyrrolidinephosphine monomers of both S,S and R,R chirality, whose copolymers are active catalysts for the asymmetric hydrogenation of N-acyl-aminocinnamic acids to produce N-acyl-α-amino acids of both R and S configuration, respectively, in high optical yields. It will be appreciated that the "S" and "R" refer respectively to Sinister and Rectus as set forth in the IUPAC Nomenclature for optically active materials.

DESCRIPTION OF THE PREFERRED EMBODIMENTS

Synthesis of Pyrrolidinephosphines

The optically active disphosphine N-t-butoxycarbonyl-2(S),4(S)-4-diphenylphosphino-2-diphenylphosphinomethylpyrrolidine (3) was synthesized from 4-hydroxy-L-pyrline by a modification of a previous procedure (Scheme 1). Achiwa, K. *J. Am. Chem. Soc.* 1976, 98, 8265. Standard esterification and and N-protection was followed by reduction of ester 6 with lithium borohydride in tetrahydrofuran to produce diol 7 in good yield. Attempts to reduce ester 6 with lithium aluminum hydride as reported failed to provide 7 in synthetically useful amounts. Tosylation and subsequent phosphination proceeded to give diphosphine 3.

Since 4-hydroxy-D-proline is not naturally available, the enantiomer of 3 is more difficult to obtain. Initially the synthetic strategy was to convert 4-hydroxy-L-proline to 4-hydroxy-D-proline by the published procedure (Scheme 2), Greenstein, J. P.; Winitz, M. "Chemistry of the Amino Acids"; John Wiley and Sons: New York, 1961, p 2037; Robinson, D. S.; Greenstein, J. P. *J. Biol. Chem.* 1952, 195, 383, and then to prepare 22 by the steps outlined for its enantiomer in Scheme 1. This procedure is long, tedious, and expensive; the overall

SCHEME I

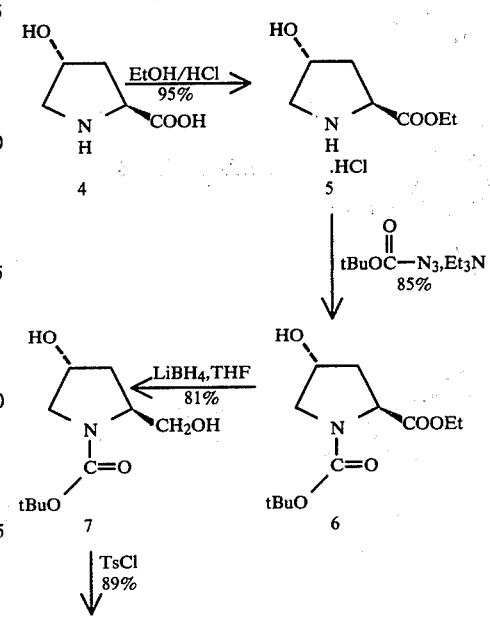

-continued
SCHEME 1

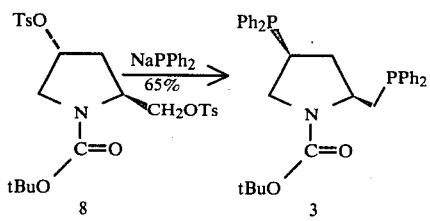

SCHEME 2

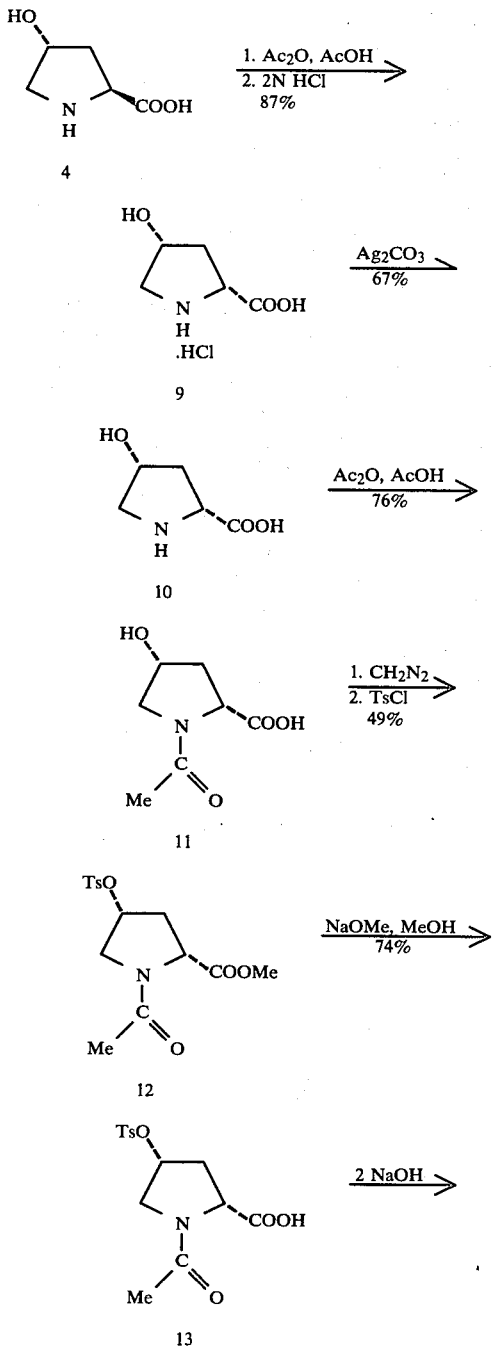

-continued
SCHEME 2

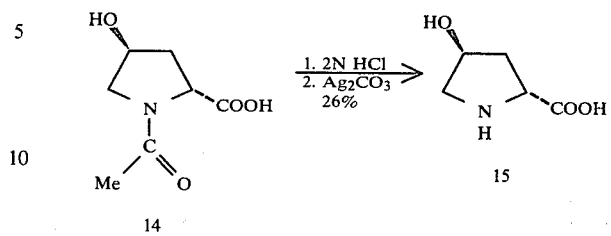

yield for the conversion of the L to D isomer was only 4.2%.

The epimerization of 4-hydroxy-L-proline (4) proceeds in high yield to the cis or allo isomer (9). This product was purified as the hydrochloride, free from the trans starting material. Removal of the hydrochloride by silver carbonate, and acylation of the free amine gave the protected amine (11) in moderate yield. The methyl ester (12) was prepared with diazomethane, and the alcohol was converted to tosylate 12. After hydrolysis of the methyl ester, the tosylate was displaced with hot base to give 14 with the desired stereo-chemistry. Olefin byproducts arising from elimination of the tosylate complicated the purification steps. Ultimately 4-hydroxy-D-proline was isolated in 26% yield.

To obtain synthetically useful amounts of the D isomer 15, large amounts of 4-hydroxy-L-proline must be used. The use of stoichiometric amounts of silver carbonate in the second and final steps makes this procedure quite expensive. In addition, molar amounts of diazomethane are employed. Despite these limitations, a small amount of 4-hydroxy-D-proline prepared as shown in Scheme 2 was ultimately carried on to the desired bisphosphine 22 by the steps outlined in Scheme 1 for is enantiomer, albeit in only a 0.2% overall yield.

A revision of the approach to the synthesis of 22 to a more direct synthetic route (Scheme 3) eliminated several problems associated with the former synthetic schemes (Schemes 1 and 2). The hydrochloride salt (9) was directly esterified with ethanol, and the amine blocked

SCHEME 3

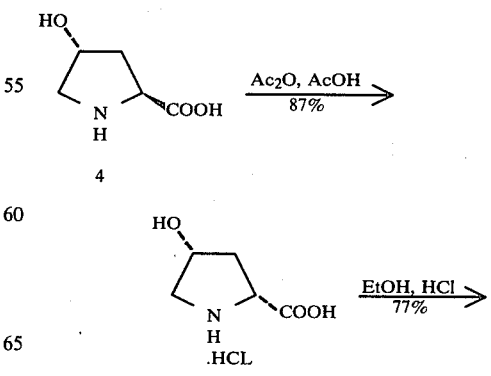

-continued
SCHEME 3

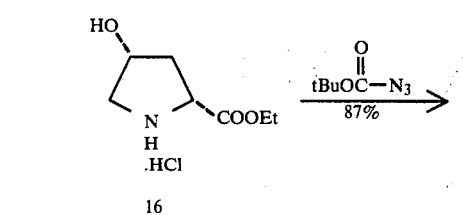
16

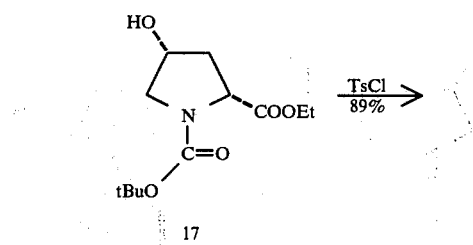
17

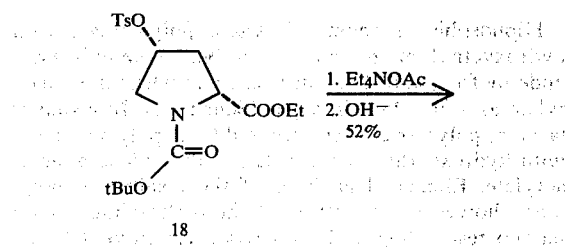
18

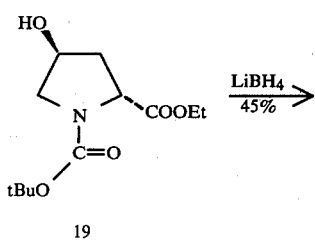
19

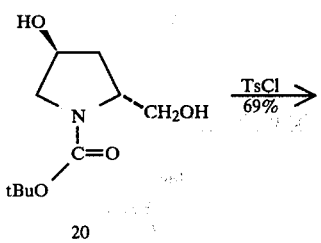
20

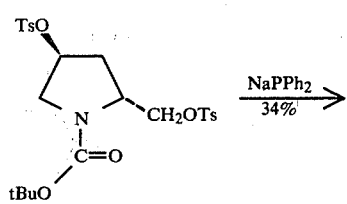
21

-continued
SCHEME 3

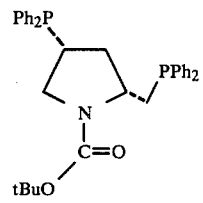
22 with the t-butoxycarbonyl groups to give 17. Tosylation of the free alcohol gave an intermediate which could be converted to the enantiomer (20) of 6 in Scheme 1. Tetraethyl ammonium acetate was used as described for an analogous conversion to displace the tosylate. Kende, A. S.; Demuth, T. P. *Tetrahedron Lett.* 1980, 21, 715. After the acetate was hydrolyzed, the free alcohol 19 was easily isolated by distillation. By using the methods developed for the synthesis of 3, its enantiomer 22 was prepared in useful amounts.

The purified phosphine (22) was used in the Rh(I) catalyzed asymmetric hydrogenation of dehydroamino acids to demonstrate its utility for the production of S amino acids. All reductions were carried out at 800 psig of hydrogen at 20° C. using neutral catalysts so that meaningful comparisons could be made with previously reported results. Achiwa, K. *J. Am. Chem. Soc.* 1976, 98, 8265. In the cases examined, comparable results were obtained, but the predominant configuration of the product was S, as expected (Table 1).

Polymer Synthesis

Acryloyl derivatives of 3 and 22 were readily prepared by removal of the protecting group with cold trifluoroacetic acid, and subsequent acylation of the free amines (Scheme 4). Using Schotten-Bauman conditions, the acrylamides were prepared in nearly 90% yield. Purification of the acryloyl derivatives proved difficult as extensive decomposition was noted on silica, alumina, and Florisil. Recrystallization from toluene/hexane gave pure monomers as white crystalline monohexanates.

TABLE 1

Hydrogenation of Dehydroamino Acids with Rh(I) 22.[a]

$$\underset{H}{\overset{R}{>}}\!\!=\!\!\underset{COOH}{\overset{NHAc}{<}} \xrightarrow[\text{EtOH/Et}_3\text{N}]{\text{Rh[I]-22}} RCH_2\overset{NHAc}{\underset{COOH}{\overset{|}{CH}}}$$

| R | optical yield[b] [config.] | lit.[c] |
|---|---|---|
| Ph— (30a) | 90S | 91R |
| AcO—C₆H₄— (30b) | 87S | 87R |

TABLE 1-continued
Hydrogenation of Dehydroamino Acids with Rh(I) 22.[a]

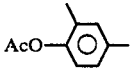

| R | optical yield[b] [config.] | lit.[c] |
|---|---|---|
| MeO—⌬—AcO (30d) | 88S | 86R |

SCHEME 4

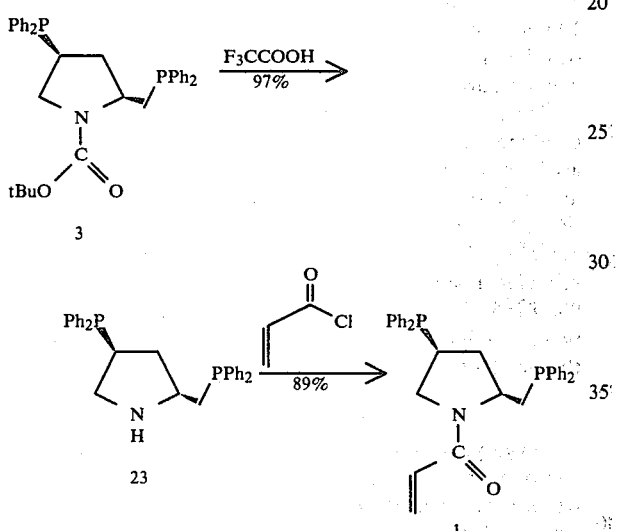

-continued
SCHEME 4

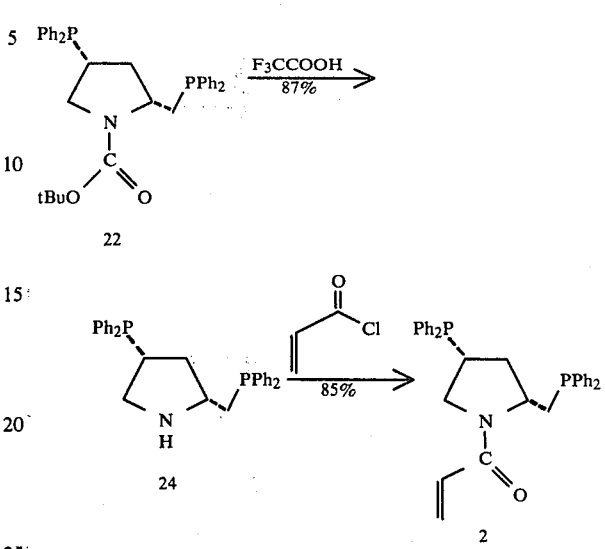

Diphosphine monomer 1 was copolymerized with hydroxyethyl methacrylate and N,N-dimethylacrylamide by free radical initiators using ethylene dimethacrylate as a crosslinking agent (Scheme 5). In a similar fashion, polymer 29 was prepared by copolymerizing 2 with hydroxyethyl methacrylate and ethylene dimethacrylate. Elemental analyses of the resulting copolymers showed incorporation of the diphosphine monomer corresponding to the monomer feed ratio of 3–5%. This relatively low percentage

SCHEME 5

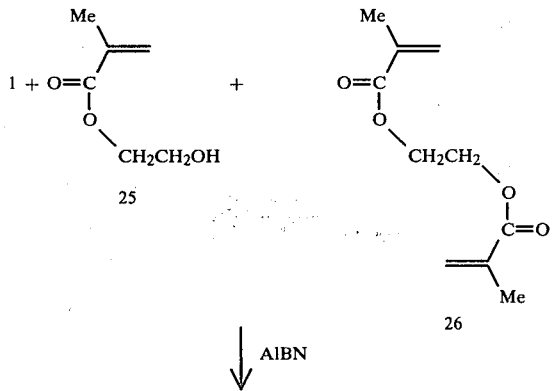

SCHEME 5 -continued

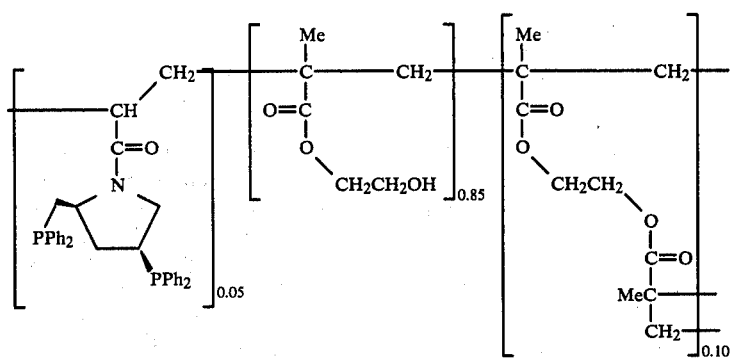

27

2 + 25 + 26 ↓ AIBN

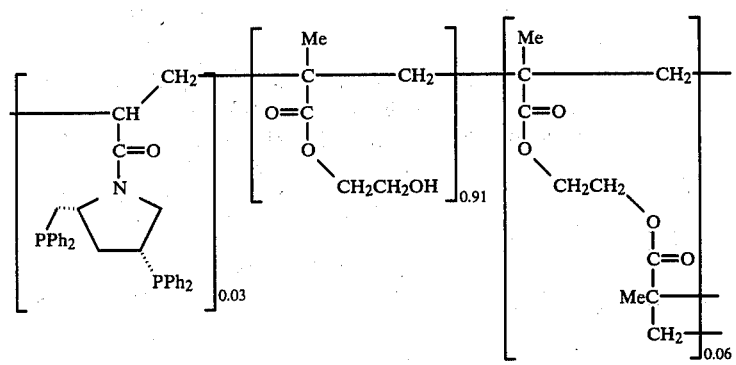

29

1 + O=C(NMe₂)CH=CH₂ + 26 ↓ AIBN

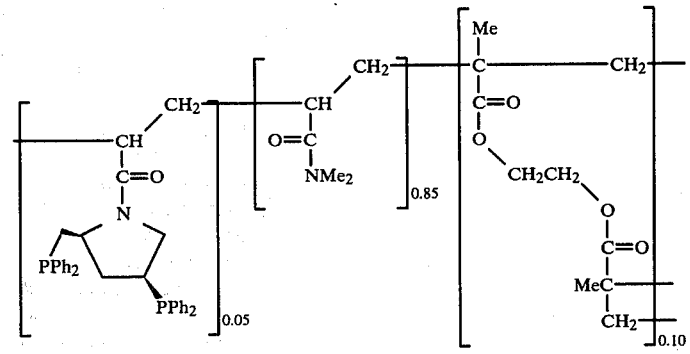

28 incorporation coupled with a crosslink density of 10% was maintained in order to insure the isolation of the catalyst sites on the polymer backbone. Polymers 27 and 29 were white free flowing powders that swelled in polar solvents such as ethanol. Polymer 28 was obtained as a pale yellow powder which swelled in solvents ranging in polarity from benzene to ethanol.

The reaction between polymers 27–29 with rhodium(I) in the form of [Rh(biallyl)Cl]₂ or [Rh(COD)Cl]₂ (COD is the abbreviation for 1,5-cyclooctadiene) gave light yellow polymer bound catalysts which were used for the hydrogenation of olefins 30a-d (Table 2). All reactions were run at 800 psig of hydrogen at 20° C. with a

TABLE 2

Hydrogenation of Dehydroamino Acids with Polymer Bound Catalysts.[a]

$$\underset{H}{\overset{R}{\diagdown}}C=C\underset{COOH}{\overset{NHAc}{\diagup}} \xrightarrow[\text{EtOH/Et}_3\text{N}]{\text{Rh(I)—polmer}} RCH_2\underset{COOH}{\overset{NHAc}{\underset{|}{C}}}H$$

30a-d

| R | polymer | optical yield[b] [config.] | lit.[c] |
|---|---|---|---|
| Ph— (30a) | 27 | 91R | 91R |
|  | 28 | 64R |  |
|  | 29 | 90S |  |
| AcO-C6H4— (30b) | 27 | 83R | 87R |
|  | 29 | 87S |  |
| HO-C6H4— (30c) | 27 | 33R | — |
|  | 28 | 35R |  |
| MeO,AcO-C6H3— (30d) | 27 | 88R | 86R |
|  | 29 | 88S |  |

[a]All reactions were run using 0.02 meq diophosphine, 0.01 meq Rh, 0.5 mmol substrate, in 15 mL EtOH, 800 psig H$_2$, 20° C. Et$_3$N:Rh = 4.
[b]See note b, Table 1.
[c]Achiwa, K. J. Am. Chem. Soc. 1976, 98, 8265, Homogeneous hydrogenation using N—t-butoxy-carbonyl-2(S),4(S)-4-diphenyl-phosphino-2-diphenylphosphinomethylpyrrolidine (3).

rhodium:diphosphine site ratio of 0.5 and a substrate:rhodium ratio of 50. The excess of phosphine sites over rhodium was maintained to insure that any phosphine sites which may have been oxidized during handling would not complex rhodium. The addition of triethylamine (6 mol % based on substrate) was essential for high optical yields. The reductions catalyzed by both polymer 27 and 29 gave the same optical yields as could be obtained with the homogeneous analogs, but the reduction of 30a with the polymer 28 rhodium(I) catalyst proceeded to give a lower optical yield than that obtained with polymer 27. It is likely that the pendent amide groups, present in large excess compared to the phosphine sites, are able to compete with phosphine sites for rhodium, thereby producing some catalytic sites which are not optically active.

As a result of practical synthetic routes for the production of pyrrolidinephosphines of both R,R and S,S chirality, both R and S amino acids can be synthesized. Polymer bound pyrrolidinephosphines were equivalent to their homogeneous analogs in their ability to yield amino acid derivatives in high optical yields. Unlike homogeneous catalysts, the polymer bound catalysts could be easily separated from the reaction mixture by filtration, and could then be reused without a significant loss in selectivity.

The choice of the proper type of polymer backbone is vital. The swelling characteristics of the polymer must be matched to the solvent system of interest so that the catalytic sites are accessible to the substrate. In order to mimic the homogeneous reaction, the polymer backbone should not interfere with the catalytic site. The use of polymers 27 and 29 with pendent alcohols showed no detectable interaction, at least as judged by optical yields. The use of polymer 28 with pendent amides led up to an overall drop in enantioselectivity due to the competition of the amides for the rhodium.

The following examples are illustrative of the present invention, but are not considered limiting thereof in any way.

All reactions were routinely performed under an inert atmosphere of nitrogen or argon. Manipulations involving phosphines dissolved in solvents were carried out in a dry box or by Schlenk techniques. Inert gasses were dried and deoxygenated by successive passage through a train of BASF De-ox catalyst and 4A molecular sieves. $^1$H NMR spectra were obtained on a Varian EM360 or on a JEOL FX-100 spectrometer with tetramethylsilane as the internal standard. $^{13}$C NMR were obtained on a JEOL FX-100 instrument with tetramethylsilane as the internal standard. $^{31}$P NMR spectra were obtained on a Nicolet NT-150 instrument or on a Bruker HX-90E spectrometer with an SPX high power amplifier, a broad band decoupler, and a model B-NC 12 computer with 85% H$_3$PO$_4$ as the external reference. Infrared spectra were obtained on a Beckman Acculab 3, or on a Perkin-Elmer 267 instrument as neat samples or potassium bromide pellets. Optical rotations were measured on a Perkin-Elmer model 241 polarimeter. Melting points are uncorrected. Elemental analyses were determined by Micro-Tech Laboratories, Skokie, Ill.

EXAMPLE 1

4-Hydroxy-L-proline, Ethyl Ester, Hydrochloride (5)

A slurry of 100 g (760 mmol) of 4-hydroxy-L-proline in 600 mL of absolute ethanol was treated with dry hydrogen chloride until homogeneous. The solution was heated to the reflux temperature for 2 h. Upon cooling in the refrigerator, the product was obtained as white needles which were filtered, washed well with ether, and dried under reduced pressure to yield 141 g (95%) of (5): mp 153°-153.5° C. (lit. mp-147°-148° C.). $^1$H NMR (DMSO d$_6$) δ1.25 (t, 3H, J=7 Hz), 4,20 (q, 2H, J=7 Hz). $^{13}$C NMR (D$_2$O) 24.1, 47.1, 63.6, 68.7, 73.8, 79.1, 177.5; IR (KBr) 3320, 1735 cm$^{-1}$.

EXAMPLE 2

N-t-Butoxycarbonyl-4-hydroxy-L-proline, Ethyl Ester (6)

A stirred mixture of 100 g (510 mmol) of 5, 75.0 mL (540 mmol) of t-butoxycarbonylazide, 150 mL of triethylamine, 500 mL of water and 500 mL of p-dioxane was heated under nitrogen to 50° C. for 15 h. The mixture was reduced in volume by one half on a rotary evaporator and extracted with four 100 mL portions of ether. The combined extracts were washed with brine, dried over magnesium sulfate and concentrated to a yellow oil under reduced pressure. Distillation of the oil under reduced pressure gave 97.5 g (69.6%) of 6 was a pale yellow oil: bp 126°-128° C. (0.05 mm); $^1$H NMR (CDCl$_3$) δ1.27 (t, 3H, J=7 Hz), 1.45 (s, 9H), 1.8-2.4 (m), 3.4-3.7 (m), 4.2 (q, 2H, J=7 Hz), 4.4-4.6 (m); $^{13}$CNMR (CDCl$_3$) δ14.2, 28.2, 28.3, 38.2, 39.0, 54.4, 57.7, 58.0, 60.9, 68.7, 69.4, 79.9, 80.1, 153.8, 154.3, 172.7, 173.0; IR (neat) 3450, 1735, 1680 cm$^{-1}$. [α]$_D^{20}$ −68.3° C. (c=2, EtOH) (lit. [α]$_D^{20}$ −67.8° C. (c=1.75, EtOH).

EXAMPLE 3

N-t-Butoxycarbonyl-4-hydroxy-L-prolinol (7)

To an ice cold solution of 50.0 g (190 mmol) of 6 in 600 mL of tetrahydrofuran was added 15.0 g (690 mmol) of lithium borohydride in one portion. The mixture was stirred at 0° C. for 1 h followed by 15 h at room temperature. The solution was cooled to 0° C. with stirring and 255 mL of water and 100 mL of 1:1 water: concentrated hydrochloric acid were added carefully. The solution was warmed until an organic phase separated. The organic phase was withdrawn and the aqueous layer was extracted with three 150 mL portions of ethyl acetate. The combined organic layers were washed with 100 mL each of 2 N sodium hydroxide, 2 N hydrochloric acid, and brine. The organic layers were dried over magnesium sulfate and evaporated under reduced pressure to an oil. The oil was kept at 0.05 mm for 24 h and then used without further purification. The yield of 7 was 33.9 g (81%). $^1$H NMR (CDCl$_3$) δ1.1–2.0 (m), 1.48 (s, 9H), 3.3–4.2 (m), 4.4 (s). $^{13}$C NMR (CDCl$_3$) δ28.4, 37.2, 54.9, 55.4, 57.7, 58.4, 63.5, 65.9, 68.6, 80.2, 154.8, 156.5; IR (neat) 3400, 1670, 1420 cm$^{-1}$.

EXAMPLE 4

N-t-Butoxycarbonyl-4-hydroxyl-L-prolinol,di-p-toluenesulfonate (8)

To a stirred solution of 11.3 g (52.0 mmol) of 7 in 300 mL of dry pyridine at 0° C. under nitrogen was added 29.7 g (156 mmol) of recrystallized p-toluenesulfonyl chloride in one portion. The mixture was stored in the refrigerator for five days. The mixture was then cooled to 0° C. and 600 mL of water was added dropwise with stirring to precipitate a white powder which was filtered, washed with water and dried under reduced pressure to yield 24.4 g (89%) of crude product. Recrystallization from 95% ethanol produced white needles of 8: mp 105°–106° C. (lit. mp 155–156?); $^1$H NMR CDCl$_3$) δ1.4 (s, 9H), 2.2 (m), 2.5 (s, 6H), 3.2–3.8 (m), 3.9–4.4 (m), 4.9–5.2 (m), 7.3–7.9 (m, 8H); $^{13}$C NMR (CDCl$_3$) δ21.2, 27.7, 33.5, 34.1, 41.4, 53.4, 68.4, 79.0, 125.4, 127.6, 130.2, 131.1, 142.4, 150.8; IR (KBr) 1690, 1600, 1450, 1360, 685, 672, 658, 620 cm$^{-1}$. $[\alpha]_D^{25}$ −25.9° (c=0.6, benzene) [lit. $[\alpha]_D^{20}$ −23° (c=0.4, benzene)]. Anal. Calcd for C$_{24}$H$_{31}$NO$_8$S$_2$: C, 54.63; H, 6.30; N, 2.65. Found: c, 54.68; H, 5.92; N, 2.62.

EXAMPLE 5

N-t-Butoxycarbonyl-2(S), 4(s)-4-diphenylphosphino-2-diphenylphosphinomethylpyrrolidine (3)

To 50 mL of liquid ammonia was added 1.15 g (50.0 mmol) of sodium cut into small pieces. Upon completion of the addition, 8.47 mL (50.0 mmol) of diphenylphosphine dissolved in 20 mL of dry tetrahydrofuran was added dropwise over 20 min. The ammonia was allowed to evaporate from the clear orange solution under a stream of nitrogen. When the solution had reached room temperature, a solution of 10.0 g (18.9 mmol) of 8 in 20 mL of dry tetrahydrofuran was added dropwise over 30 min. The mixture was allowed to stir at room temperature for 18 h. The solution was treated with methanol to destroy the excess anion and filtered. The filter cake was washed with benzene and the filtrate was concentrated under reduced pressure. The remaining oil was crystallized from 100 mL absolute ethanol after standing in the refrigerator for 48 h. The reaction yielded 6.15 g (59%) of white crystalline 3. An addition 0.47 g (4.5%) was obtained through concentration of the solution and further cooling: mp 103.5°–105° C. (lit. mp 104°–105° C.); $^1$H NMR (CDCl$_3$) δ1.2–1.6 (m), 1.4 (s, 9H), 1.8–2.2 (m), 2.7–3.2 (m), 7.2–7.4 (br s, 20H); $^{13}$C NMR (CDCl$_3$) δ28.4 (s), 35.0 (d, J=9 Hz), 37.5 (d, J=15 Hz), 49.7 (s), 50.7 (s), 55.8 (dd, J=22, 7 Hz), 79.4 (s), 128.0–129.4 (4 peaks), 131.5–133.3 (9 peaks), 136.0–136.8 (4 peaks), 138.3 (s), 138.7 (s), 153.5 (s); IR (KBr) 1680, 1480, 1435, 1395, 1175, 1125, 1100, 740, 695 cm$^{-1}$. $[\alpha]_D^{25}$ −38.9° (c=0.6, benzene) [lit.[6] $[\alpha]_D^{20}$ −36° (c=0.6, benzene)]. Anal. Calcd for C$_{34}$H$_{37}$NO$_2$P$_2$: C, 73.76; H, 6.73; N, 2.53; P, 11.19. Found: C, 73.44; H, 6.76; N, 2.41; P, 10.49.

EXAMPLE 6

Allo-4-hydroxy-D-proline, Hydrochloride 9

A solution of 1020 g (10 mol) of acetic anhydride in 3 L of glacial acetic acid was heated to 50° C. and 274 g (1.89 mol) of 4-hydroxy-L-proline was added in one portion. Heating was continued until the reflux temperature was reached, and the solution was held at reflux for 5.5 h. After cooling, the solvent was removed in vacuo giving a thick oil. The oil was dissolved in 3.5 L of 2 N hydrochloric acid and was then heated to the reflux temperature for 3 h. The solution was treated with charcoal while hot and then filtered through Celite. While concentrating the solution by rotary evaporation, white needles formed that were collected by suction filtration. The needles were dried under reduced pressure to give 240 g (1.4 mol, 75%) of the hydrochloride salt: mp 161°–163° C.; $^1$H NMR (D$_2$O, external Me$_4$Si) δ2.3–3.0 (m, 2H), 3.5 (d, 2H, J=2.5 Hz), 4.4–4.8 (m, 2H): $^{13}$C NMR (DMSO d$_6$) δ171.0, 68.9, 58.3, 53.7, 37.9; IR (KBR) 3430, 3030, 1710, 1585, 1380, 1280, 1260, 965, 720, 665 cm$^{-1}$. The filtrate was further concentrated to give an addition 39 g (0.22 mol, 12%) of 9.

EXAMPLE 7

Allo-4-hydroxy-D-proline 10

The free amine was prepared from the hydrochloride salt as described in Robinson, D. S.; Greenstein, J. P. *J. Biol. Chem.* 1952, 195, 383, to yield 140 g (1.13 mol, 67%) of 10: mp 252°–257° C. d; $^1$H NMR (D$_2$O) δ2.4–3.1 (m, 2H), 3.4 (d, 2H, J=2.5 Hz), 3.9–4.7 (m, 2H). $[\alpha]_D^{25}$=+60.3° (c=2.6, H$_2$O) [lit. $[\alpha]_D$=+59.5° (c=2, H$_2$O)].

EXAMPLE 8

N-Acetyl-allo-4-hydroxy-D-proline 11

The amine was protected as described in Robinson, D. S.; Greenstein, J. P. *J. Biol. Chem.* 1952, 195, 383, to yield 26 g (0.15 mol, 76%) of pure 11: mp 145.5°–147° C. (lit. 145.5° C.); $^1$H NMR (D$_2$O, external Me$_2$Si) δ2.0 (s, 3H), 2.1–2.6 (m, 2H), 4.2–2.7 (m, 2H). $[\alpha]_D^{22}$=+91.0° (c=2, H$_2$O) [lit. $[\alpha]_D^{25}$=+91.0° (c=2, H$_2$O)].

EXAMPLE 9

N-Acetyl-p-toluenesulfonyl-allo-4-hydroxy-D-proline, Methyl Ester 12

The methyl ester was prepared as described in Robinson, D. S.; Greenstein, J. P. *J. Biol. Chem.* 1952, 195, 383, to yield 130 g (0.38 mol, 49%) of white needles: mp 150°–152° C. (lit. 143.5° C.); $^1$H NMR (CDCl$_3$) δ2.0 (s, 3H), 2.2–2.8 (m, 5H), 3.5–3.8 (m, 5H), 4.2–4.7 (m, 1H), 7.1-7.7 (m, 4H). $[\alpha]_D^{22} = +36.7°$ (c=3.1, EtOH) [lit. $[\alpha]_D^{25} = +32.0°$ (c=1, EtOH)].

EXAMPLE 10

N-Acetyl-p-toluenesulfonyl-allo-4-hydroxy-D-proline 13

The ester was hydrolyzed as described in Robinson, D. S.; Greenstein, J. P. *J. Biol. Chem.* 1952, 195, 383, to give 67.2 g (0.20 mol, 74%) of the free acid 13: mp 149°-151° C. (lit. 143.5° C.); $^1$H NMR (CDCl$_3$) $\delta$2.1 (s, 3H), 2.2-2.7 (m, 2H), 2.4 (s, 3H), 3.6-3.6 (m, 2H), 4.3-4.7 (m, 1H), 4.8-5.2 (m, 1H), 7.1-7.8 (m, 4H). $[\alpha]_D^{20} = +30.5°$ (c=0.8, EtOH) [lit. $[\alpha]_D^{25} = +30.5°$ (EtOH)]; Greenstein, J. P.; Winitz, M. "Chemistry of the Amino Acids"; John Wiley and Sons: New York, 1961, p 2037.

EXAMPLE 11

4-Hydroxy-D-proline 15

The amino acid was prepared as described in Robinson, D. S.; Greenstein, J. P. *J. Biol. Chem.* 1952, 195, 383, from 13 to give 5.1 g (39 mmol, 26%) of 4-hydroxy-D-proline as white crystals. $^1$H NMR (D$_2$O, external Me$_4$Si) $\delta$1.7-2.6 (m, 2H), 3.3 (m, 2H), 4.1-4.7 (m, 2H). $[\alpha]_D^{21} = +79.3°$ c=2, H$_2$O) [lit. $[\alpha]_D^{25} = 76°$ (c=2, H$_2$O)].

EXAMPLE 12

4-Hydroxy-D-proline, Ethyl Ester, Hydrochloride

The ester was prepared as described for the L isomer (5) to yield 3.6 g (19 mmol, 57%): mp 157°-158.5; $^1$H NMR (DMSO) $\delta$1.25 (t, 3H, J=7 Hz), 4.20 (g, 2H, J=7 Hz).

EXAMPLE 13

N-t-Butoxycarbonyl-4-hydroxy-D-proline, Ether Ester 19 a. From 4-hydroxy-D-proline, ethyl ester, hydrochloride.

The t-BOC derivative was prepared as described for the corresponding L isomer to yield 4.0 g (15 mmol, 81%): bp 130° C., (0.05 mm); $^1$H NMR (CDCl$_3$) $\delta$1.2 (t, 3H, J=7 Hz), 1.5 (s, 9H), 1.8-2.5 (m, 2H), 3.4-3.7 (m, 2H), 4.1 (q, 2H, J=7 Hz), 4.3-4.5 (m, 2H). $[\alpha]_D^{20} = 70.4°$ (c=2, ethanol).

b. From 18.

To 200 mL of benzene was added 28.7 g (110 mmol) of tetraethylammonium acetate tetrahydrate. The water was azeotropically removed overnight. To the mixture at the reflux temperature was added 39.7 g (100 mmol) of tosylate 18. After 1.5 h, the reaction was cooled to room temperature. Platelets of tetraethylammonium tosylate formed and were removed by suction filtration. The benzene portions were evaporated to dryness giving an oil. The oil was dissolved in 200 mL of methanol and cooled to 0° C. To the ice cold solution was carefully added 160 mL of 1 N sodium hydroxide. After stirring for 75 min, the pH was adjusted to 7 by adding concentrated hydrochloric acid dropwise. The solution volume was reduced by one half by rotary evaporation, and was then extracted with three 100 mL portions of chloroform. The combined extracts were dried over magnesium sulfate, filtered, and evaporated to dryness. The resulting yellow oil was distilled under reduced pressure (147°-148° C./0.15 mm) to give 13 g (52 mmol, 52%) of 19 as a thick, pale yellow oil, identical to that obtained by method a. The forerun in the distillation contained olefin products corresponding to acetate or tosylate elimination.

EXAMPLE 14

N-t-Butoxycarbonyl-4-hydroxy-D-prolinol 20

The diol was prepared by the same procedure used to prepare the L isomer 7. Yield: 4.8 g (22 mmol, 45%); $^1$H NMR (CDCl$_3$) $\delta$1.45 (s, 9H), 1.8-2.3 (m, 1H), 3.2-4.3 (m, 8H), 4.7 (br, OH).

EXAMPLE 15

N-t-Butoxycarbonyl-4-hydroxy-D-prolinol, di-p-toluenesulfonate 21

The ditosylate was prepared by the method used for the L isomer 8. Yield: 8.0 g (15 mmol, 69%): mp 104°-106° C.; $^1$H NMR (CDCl$_3$) $\delta$1.3 (s, 9H), 2.2 (m, 2H), 2.4 (s, 6H), 3.1-3.7 (m, 2H), 3.9-4.4 (m, 3H), 4.8-5.1 (m, 1H), 6.9-7.7 (m, 8H). $[\alpha]_D^{22} = +27.2°$ (c=1.94, benzene).

EXAMPLE 16

N-t-Butoxycarbonyl-2(R), 4(R)-4-diphenylphosphino-2-diphenylphosphinomethylpyrrolidine 22

The bisphosphine was prepared as described for the (S,S) isomer 3. Yield: 3.6 g (6.5 mmol, 34%): mp 103°-104° C.; $^1$H NMR (CDCl$_3$) $\delta$1.2-1.6 (m, 1H), 1.4 (s, 9H), 1.8-2.2 (m, 4H), 2.7-3.2 (m, 3H), 7.2-7.4 (br, s, 20H); $^{31}$P NMR (CDCl$_3$) $\delta$ −7.3, −21.8. $[\alpha]_D^{20} = -36.5°$ (c=0.6, benzene). Anal. Calcd for C$_{34}$H$_{37}$NO$_2$P$_2$: C, 73.76; H, 6.73; N, 2.53; P, 11.19. Found: C, 74.06; H, 6.87; N, 2.65; P, 11.12.

EXAMPLE 17

Allo-4-hydroxy-D-proline, Ethyl Ester, Hydrochloride 16

A slurry of 100 g (0.6 mol) of 9 in 500 mL of absolute ethanol was treated with dry hydrochloric acid gas until complete dissolution of the acid had occurred. The solution was then heated to the reflux temperature for 5 h, and then was slowly cooled. The white needles which formed were collected by suction filtration and dried under reduced pressure to give 90 g (0.46 mol, 77%) of ester 16: mp 155°-156° C.; $^1$H NMR (DMSO d$_6$) $\delta$1.2 (t, 3H, J=7 Hz), 1.8-2.6 (cm, 3H), 3.15 (d, 2H, J=3 Hz), 4.1 (q, 2H, J=7 Hz), 4.1-4.5 (m, 2H); $^{13}$C NMR (DMSO d$_6$) $\delta$169.2, 68.6, 62.5, 57.9, 53.3, 38.3, 14.4; IR (KBr) 3250, 1717 cm$^{-1}$.

EXAMPLE 18

N-t-Butoxycarbonyl-allo-4-hydroxy-D-proline, Ethyl Ester 17

To a solution of 89 g (0.46 mol) of 16 in 600 mL of a 1:1 mixture of dioxane:water were added 150 mL of triethylamine, and 68 mL of t-butoxycarbonyl-azide. The mixture was heated to 50° C. for 15 h. The volume of of solvent was reduced by one half by rotary evaporation, and the resulting solution was extracted with four 100 mL portions of ether. The combined ether layers were washed with saturated sodium chloride solution and then dried over magnesium sulfate. The solution was filtered and evaporated to give a thick oil, which after distillation (118°-119° C., 0.15 mm) gave 103 g (0.40 mol, 87%) of 17 as a thick, pale yellow oil: $^1$H NMR (CDCl$^3$) $\delta$1.2 (t, 3H, J=7 Hz), 1.4 (s, 9H), 1.9–2.4 (m, 2H), 3.4 (m, 2H), 3.7–4.3 (m, 2H), 4.1 (q, 2H, J=7 Hz); $^{13}$C NMR (CDCl$_3$) δ173.9, 154.1, 153.6, 80.1, 70.6, 69.6, 61.4, 58.0, 55.3, 54.9, 38.6, 37.8, 28.3, 14.1; IR (neat) 3450, 1745, 1700 cm$^{-1}$. $[\alpha]_D^{22}=+15.4°$ (c=3.3, ethanol). Anal. Calcd for C$_{12}$H$_{21}$NO$_5$: C, 55.58; H, 8.16; N, 5.40. Found: C, 55.53; H, 8.40; n, 5.34.

EXAMPLE 19

N-t-Butoxycarbonyl-allo-4-hydroxy-D-proline, Ethyl Ester, p-toluenesulfonate 18

To a solution of 80 g (0.31 mol) of alcohol 17 in 300 mL of dry pyridine at 0° C., was added 65.2 g (0.34 mol) of p-toluenesulfonyl chloride in three portions. After an additional hour at 0° C., the solution was allowed to warm to room temperature. After 48 h, the tosylate was precipitated by slowly adding 1 L of water to the pyridine solution at 0° C. over 4 h. The solid was collected by suction filtration, washed well with water, and dried under reduced pressure. The solid was recrystallized from 300 mL of absolute ethanol to give 110 g (0.28 mol, 89%) of 18 as white crystals: mp 74°–75.5° C.; $^1$H NMR (CDCl$_3$) δ1.25 (t, 3H, J=7 Hz), 1.4 (s, 9H), 2.2–2.4 (m, 2H), 2.4 (s, 3H), 3.6 (m, 2H), 4.2–4.4 (m, 1H), 4.1 (q, 2H, J=7 Hz), 4.8–5.2 (m, 1H), 7.1–7.8 (m, 4H); $^{13}$C NMR CDCl$_3$) δ170.1, 170.6, 153.3, 153.0, 144.9, 133.4, 129.8, 127.3, 79.9, 79.3, 78.1, 61.0, 57.4, 52.0, 51.7, 36.8, 35.9, 28.1, 21.4, 14.1; IR (KBr) 1760, 1700, 1605, 1400, 1375, 900, 740, 660 cm$^{-1}$. $[\alpha]_D^{22}=+17.8°$ (c=2.35, ethanol). Anal. Calcd for C$_{17}$H$_{27}$NO$_7$S: C, 55.19; H, 6.58; N, 3.39. Found: C, 55.20; H, 6.64; N, 3.33.

EXAMPLE 20

2(S), 4(S)-4-Diphenylphosphino-2-diphenylphosphinomethylpyrrolidine 23

To 100 mL of ice cold trifluoroacetic acid under nitrogen was added 12.1 g (21.8 mmol) of 31 in one portion. The mixture was stirred at 0° C. for 30 min and the trifluoroacetic acid was removed under reduced pressure. The residue was taken up in 100 mL of dichloromethane and washed with 100 mL of water, two 100 mL portions of 2 N sodium hydroxide, and two 50 mL portions of brine. The organic layer was dried over potassium carbonate and evaporated under reduced pressure to yield 9.87 g (99.6%) of 23 as a pale yellow oil which crystallized after 20 h at 0.5 mm: mp 73°–75° C. (lit. 103–104?); $^1$H NMR (CDCl$_3$) δ1.2–1.6 (m), 2.0–2.5 (m), 2.7–3.2 (m), 7.2–7.6 (m); $^{13}$C NMR (CDCl$_3$) δ35.0 (d, J=13 Hz), 36.5 (dd, J=10, 1.5 Hz), 38.9 (dd, J=18, 7 Hz), 50.4 (d, J=24 Hz), 57.7 (dd, J=16, 7 Hz), 127.9–128.8 (8 peaks), 131.9–133.2 (8 peaks), 137.4–138.4 (7 peaks); IR (KBr) 1480, 1430, 740, 695 cm$^{-1}$. $[\alpha]_D^{25}=-15.65°$ [(c=1.08, benzene) lit. $[\alpha]_D^{20}=-7°$ (c=1.84, benzene)]. Anal. Calcd for C$_{29}$H$_{29}$NP$_2$: C, 76.80; H, 6.44; N, 3.09; P, 13.66. Found: C, 76.23; H, 6.21; N, 2.91; P, 13.73.

EXAMPLE 21

2(R), 4(R)-4-Diphenylphosphino-2-diphenylphosphinomethylpyrrolidine (24)

The (R,R) isomer 24 was prepared as described for the (S,S) isomer 23. Yield: 2.1 g (4.7 mmol, 87%). $^1$N NMR (CDCl$_3$) δ1.2–1.6 (m, 1H), 2.0–2.5 (m, 4H), 2.7–3.2 (m, 3H), 7.0–7.5 (m, 20H); IR (neat) 3300, 1655, 1585, 1480, 1430, 725, 690 cm$^{-1}$.

EXAMPLE 22

N-Acryloyl-2(S),4(S)-4-diphenylphosphino-2-diphenylphosphinomethylpyrrolidine (1)

To a well stirred, two phase mixture of 7.20 g (15.8 mmol) of 23 in 100 mL of toluene and 100 mL of 2 N sodium hydroxide at 0° C. was added 1.87 g (20.6 mmol) of acryloyl chloride in 50 mL of toluene dropwise over 30 min. The mixture was stirred for an additional 15 min at 0° C. and the layers were separated. The aqueous phase was extracted with two 100 mL portions of benzene and the combined organic layers were washed with 50 mL of 2 N hydrochloric acid and two 50 mL portions of brine. The solution was dried over magnesium sulfate and concentrated under reduced pressure to a pale yellow oil which solidified at 0.5 mm to yield 7.20 g (89%) of crude 1. Recrystallization from toluene/hexane (1:10) gave white needles of 1 as the mono hexane solvate (by NMR). Dissolution in chloroform and reevaporation provided solvent free material; mp broad with extensive decomposition; $^1$H NMR (CDCl$_3$) δ1.9–2.5 (m), 3.2–3.7 (m), 5.5–5.9 (m), 6.0–6.3 (m), 7.2–7.7 (m); $^{13}$C NMR (CDCl$_3$) 33.1 (d, J=14 Hz), 35.7 (d, J=9 Hz), 36.8 m, not well resolved), 51.1 (d, J=28 Hz), 56.2 (dd, J=20, 4 Hz), 127.1, 127.7–129.2 (11 peaks), 131.4–133.6 (9 peaks), 135.4–136.8 (5 peaks), 138.4, 138.9, 163.2, 163.8; IR (KBr) 1650, 1610, 1480, 1430, 740, 695 cm$^{-1}$. $[\alpha]_D^{20}=25.7°$ (c=1.04, benzene). Anal. Calcd for C$_{32}$H$_{31}$NOP$_2$: C, 75.72; H, 6.16; P, 12.21. Found: C, 75.43; H, 6.09, P, 11.89.

EXAMPLE 23

N-Acryloyl-2(R),4(R)-diphenylphosphino-2-diphenylphosphinomethylpyrrolidine (2)

The (R,R) acrylamide was prepared as described for the (S,S) isomer 1. Yield: 0.54 g (1.1 mmol, 28%); $^1$H NMR (CDCl$_3$) δ1.9–2.5 (m, 4H), 3.2–3.7 (m, 4H), 5.5–5.9 (m, 1H), 6.0–6.3 (m, 2H), 7.2–7.7 (m, 20H); $^{13}$C NMR (CDCl$_3$) δ163.9, 163.4, 139.0, 138.5, 137.4, 135.6 (5 peaks), 133.6–130.3 (8 peaks), 128.9–127.0 (6 peaks), 56.9–55.8 (4 peaks), 51.8–48.6 (4 peaks), 38.0–32.9 (9 peaks); $^{31}$P NMR (CDCl$_3$) δ−6.4, −8.5, −21.9, −22.3; IR (KBr) 1650, 1615, 1480, 1430, 735, 690 cm$^{-1}$. $[\alpha]_D^{22}=+26.1°$ (c=1.04, benzene). Anal. Calcd for C$_{32}$H$_{31}$NOP$_2$: C, 75.72; H, 6.16. Found: C, 75.91; H, 6.33.

EXAMPLE 24

Materials for Hydrogenation Reactions

Ethanol was dried and degassed by distillation from magnesium ethoxide under argon. Triethylamine was dried and degassed by distillation from calcium hydride under argon. Tetrahydrofuran was distilled from sodium-benzophenone ketyl under argon. Hydrogen was purchased from Airco and used as received. α-Acetamidocinnamic acid (30a) was prepared by a published procedure, Herbst, R. M.; Slemin, D. "Organic Synthesis", Collect. Vol. II; Wiley: New York, 1943; p 1. Substituted cinnamic acids 30b-d were prepared in a similar fashion from the appropriate aldehydes.

EXAMPLE 25

Copolymerization of 1 and 2 with Hydroxyethyl Methacrylate and Ethylene Dimethyacrylate. Preparation of 27 and 29

The following procedure illustrated for the preparation of polymer 27 was also used for the preparation of 29.

To a resin kettle equipped with an efficient overhead stirrer, condenser, and nitrogen inlet was added 50 mL of distilled, thiophene free benzene which was heated to 65° C. An additional 10 mL of benzene was used to dissolve 2.179 g (16.75 mmol) of freshly distilled hydroxyethyl methacrylate, 0.390 g (1.97 mmol) of ethylene dimethacrylate and 0.500 g (0.985 mmol) of 1. The monomer solution was degassed via two freeze-pump-thaw cycles and added to the resin kettle. The polymerization was initiated by the addition of 50 mg of azobisisobutyronitrile (AIBN). The mixture was stirred at 65° C. for 12 h, filtered under argon in the dry box and the filter cake was dried under reduced pressure to yield 2.62 g (85%) of 27 as a white powder. The elemental analyses for polymers 27 and 29 appear in Table 3.

EXAMPLE 26

Copolymerization of 1 with N,N-dimethylacrylamide and Ethylene Dimethacrylate. Preparation of 28

To a resin kettle equipped with an efficient stirred, condenser, and nitrogen inlet was added 30 mL of distilled, thiophene free benzene which was heated to 70° C. An additional 10 mL of benzene was used to dissolve 1.660 g (16.75 mmol) of N,N-dimethylacrylamide, 0.390 g (1.97 mmol) of ethylene dimethacrylate, and 0.500 g (0.985 mmol) of 1. The solution was degassed via two freeze-pump-thaw cycles and added to the resin kettle. The polymerization was initiated by the addition of 100 mg of AIBN. After 2.5 h at 70° C., the mixture set to a yellow gel. The mixture was cooled and treated with 100 mL of degassed hexane to shrink the gel. The insoluble material was filtered in the dry box and dried under reduced pressure to yield 2.36 g (92%) of 28 as a pale yellow powder. The elemental analysis for polymer 28 appears in Table 3.

TABLE 3

Elemental Analyses of Polymers 27-29

| Polymer | % P | mol % $P_2$ | mmol $P_2$/g |
|---|---|---|---|
| 27 | 1.59 | 3.75 | 0.25 |
| 28 | 2.14 | 4.48 | 0.29 |
| 29 | 1.04 | 2.45 | 0.17 |

EXAMPLE 27

General Procedure for Assymmetric Hydrogenation Using Homogeneous Pyrrolidinephosphine-Rhodium(I) Catalysts A typical hydrogenation was carried out as follows. To a glass lined bomb was added 4 mg (0.01 mmol) of -dichlorobis(1, 5-hexadiene) dirhodium(I), 12 mg (0.022 mmol) of 22 and 2 mmol of substrate. The bomb was brought into the dry box and 15 mL of absolute ethanol and 8.3 L of triethylamine were added. The bomb was sealed under argon and then pressurized to 800 psig with hydrogen. The bomb was placed in a constant temperature bath maintained at 20° C. and stirred magentically. The reactions were worked up as described in J. Am. Chem. Soc., 1978, 100, 264. The product was analyzed by $^1$H NMR. The integration between product and starting material N-acetyl peaks was used to determine conversion. The optical yield was determined by polarimetry. Results are reported in Table 1.

EXAMPLE 28

General Procedure for Asymmetric Hydrogenation Using Polymer Supported Catalysts A typical hydrogenation was carried out as follows. To an argon filled flask was added 68 mg (0.018 meq diphosphine) of 27, 2 mg (0.01 mmol Rh) of μ-dichlorobis(1,5-hexadiene)dirhodium(I) and 15 mL of ethanol. The mixture was stirred for 1 h and then filtered under argon to give the yellow polymer bound catalyst. The catalyst was transferred under argon to a glass lined bomb equipped with magnetic stirring. After addition of 0.5 mmol of substrate, 15 mL of ethanol and 5.0 μL of triethylamine, the bomb was pressurized to 800 psig with hydrogen and stirred at 20° C. Work-up consisted of filtration to remove the catalyst and evaporation of the solvent. When the reaction solvent was ethanol, the residue was taken up in 10 mL of nitromethane and reevaporated. This removes the last trace of ethanol. The products were analyzed by $^1$H NMR. The integration between product and starting material N-acetyl peaks was used to determine conversion. The optical yields were determined by polarimetry. The results are listed in Table 2.

I claim:

1. The method of forming a catalyst for the asymmetric hydrogenation of N-acyl-α-amino acids of both R and S configuration, respectively, in high optical yields which comprises the step of copolymerization of N-acryloyl-2(S),4(S)-4-diphenylphosphino-2-diphenyllphosphinomethylpyrrolidine or N-acryloyl-2(R),4(R)-4-diphenylphosphino-2-diphenylphosphinomethylpyrrolidine with hydrophilic vinyl comonomers and a divinyl monomer, in the presence of a free radical initiator to yield a copolymer, and as a further step exchanging rhodium(I) onto the copolymer at the phosphine sites, while maintaining an excess of phosphine sites over rhodium, and in the presence of triethylamine, said rhodium(I) being in the form of [Rh(bially)Cl]$_2$ or [Rh(COD)Cl]$_2$.

2. The catalyst formed by the method of claim 1.

* * * * *